(12) United States Patent
Chen

(10) Patent No.: US 9,192,306 B2
(45) Date of Patent: *Nov. 24, 2015

(54) PHOTOACOUSTIC IMAGING DEVICES AND METHODS OF IMAGING

(71) Applicant: STC.UNM, Albuquerque, NM (US)

(72) Inventor: Jingkuang Chen, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,933

(22) Filed: Sep. 9, 2013

(65) Prior Publication Data

US 2014/0012125 A1 Jan. 9, 2014

Related U.S. Application Data

(63) Continuation of application No. 12/747,428, filed as application No. PCT/US2008/086206 on Dec. 10, 2008, now Pat. No. 8,529,454.

(60) Provisional application No. 61/007,023, filed on Dec. 10, 2007, provisional application No. 61/032,947, filed on Feb. 29, 2008.

(51) Int. Cl.
A61B 5/00 (2006.01)
A61B 5/02 (2006.01)
(Continued)

(52) U.S. Cl.
CPC ............ *A61B 5/0095* (2013.01); *A61B 5/0086* (2013.01); *A61B 5/02007* (2013.01);
(Continued)

(58) Field of Classification Search
CPC ........... A61B 2562/028; A61B 5/0086; A61B 5/0095; A61B 5/02007; A61B 8/0833; A61B 8/12; A61B 8/4472; A61B 8/4483; A61B 8/483; Y10T 29/49826

USPC ......... 600/459, 407, 437, 347, 439, 443, 463, 600/547; 385/88, 31, 38, 115–119, 89, 47; 437/60, 901, 919; 356/73; 29/594, 29/609.1; 250/227.11, 227.24, 227.2

See application file for complete search history.

(56) References Cited

U.S. PATENT DOCUMENTS 6,406,196 B1 6/2002 Uno et al.
6,498,942 B1 12/2002 Esenaliev et al.
(Continued)

FOREIGN PATENT DOCUMENTS

CN 1191023 A 8/1998
CN 1575770 A 2/2005
(Continued)

OTHER PUBLICATIONS

U.S. Appl. No. 12/747,428, Non Final Office Action mailed Oct. 3, 2012, 15 pgs.
(Continued)

*Primary Examiner* — Michael Rozanski
(74) *Attorney, Agent, or Firm* — Schwegman Lundberg & Woessner, P.A.

(57) ABSTRACT

A photoacoustic medical imaging device may include a substrate, an array of ultrasonic transducers on the substrate, at least one groove etched on the substrate, at least one optical fiber, and at least one facet. Each optical fiber is disposed in one of the grooves. Each facet is etched in one of the grooves and coated with a layer of metal having high infrared reflectivity. Each optical fiber is configured to guide infrared light from a light source through the fiber and toward the respective facet. The facet is configured to reflect the infrared light toward a target.

20 Claims, 9 Drawing Sheets

(51) Int. Cl.
*A61B 8/12* (2006.01)
*A61B 8/00* (2006.01)
*A61B 8/08* (2006.01)

(52) U.S. Cl.
CPC .............. *A61B 8/12* (2013.01); *A61B 8/4472* (2013.01); *A61B 8/4483* (2013.01); *A61B 8/483* (2013.01); *A61B 8/0833* (2013.01); *A61B 2562/028* (2013.01); *Y10T 29/49826* (2015.01)

(56) References Cited

U.S. PATENT DOCUMENTS

| | | | |
|---|---|---|---|
| 6,979,292 | B2 | 12/2005 | Kanayama et al. |
| 7,956,510 | B2 * | 6/2011 | Huang ............... 310/309 |
| 8,529,454 | B2 | 9/2013 | Chen |
| 2002/0168144 | A1 | 11/2002 | Chen et al. |
| 2005/0004458 | A1 | 1/2005 | Kanayama et al. |
| 2005/0187471 | A1 | 8/2005 | Kanayama et al. |
| 2007/0014527 | A1 * | 1/2007 | Colgan et al. ............ 385/137 |
| 2007/0093702 | A1 | 4/2007 | Yu et al. |
| 2007/0287912 | A1 | 12/2007 | Khuri-Yakub et al. |
| 2008/0141521 | A1 * | 6/2008 | Ladabaum et al. ........... 29/594 |
| 2008/0177183 | A1 * | 7/2008 | Courtney et al. ........... 600/463 |
| 2009/0264768 | A1 * | 10/2009 | Courtney et al. ........... 600/463 |
| 2010/0268058 | A1 | 10/2010 | Chen |

FOREIGN PATENT DOCUMENTS

| | | | |
|---|---|---|---|
| EP | 1493380 | A1 | 1/2005 |
| WO | WO-2005/067786 | A1 | 7/2005 |
| WO | WO-2006/061829 | A1 | 6/2006 |
| WO | WO-2009/076427 | A1 | 6/2009 |

OTHER PUBLICATIONS

U.S. Appl. No. 12/747,428, Notice of Allowance mailed May 9, 2013, 8 pgs.
U.S. Appl. No. 12/747,428, Preliminary Amendment filed Jun. 10, 2010, 3 pgs.
U.S. Appl. No. 12/747,428, Response filed Jan. 2, 2013 to Non Final Office Action mailed Oct. 3, 2012, 12 pgs.
Chinese Application Serial No. 200880123985.X, Office Action mailed Feb. 16, 2013, (w/ English Translation), 8 pgs.
Chinese Application Serial No. 200880123985.X, Response filed Apr. 26, 2013 to Office Action mailed Feb. 16, 2013, (w/ English Translation of Claims), 10 pgs.
Chinese Application Serial No. 200880123985.X, Response filed Oct. 17, 2012 to Office Action mailed Apr. 5, 2012, (w/ English Translation of Claims), 13 pgs.
Chinese Application Serial No. 200880123985.X, Office Action mailed Apr. 5, 2012, (w/ English Translation), 13 pgs.
European Application Serial No. 08860441.8, Amendment filed Feb. 1, 2012, 16 pgs.
European Application Serial No. 08860441.8, Amendment filed May 3, 2012, 16 pgs.
European Application Serial No. 08860441.8, European Search Report mailed Jul. 7, 2011, 6 pgs.
European Application Serial No. 08860441.8, Non Final Office Action mailed Jul. 27, 2011, 1 pg.
International Application Serial No. PCT/US08/86206, International Search Report mailed Jan. 27, 2009, 1 pg.
International Application Serial No. PCT/US2008/086206, International Preliminary Report on Patentability mailed Jun. 15, 2010, 5 pgs.
International Application Serial No. PCT/US2008/086206, Written Opinion mailed Jan. 27, 2009, 4 pgs.
Chen, Jingkuang, et al., "A Monolithic Three-Dimensional Ultrasonic Transducer Array for Medical Imaging", *Journal of Microelectromechanical Systems* vol. 16. No. 5, (Oct. 2007), 1015-1024.

* cited by examiner

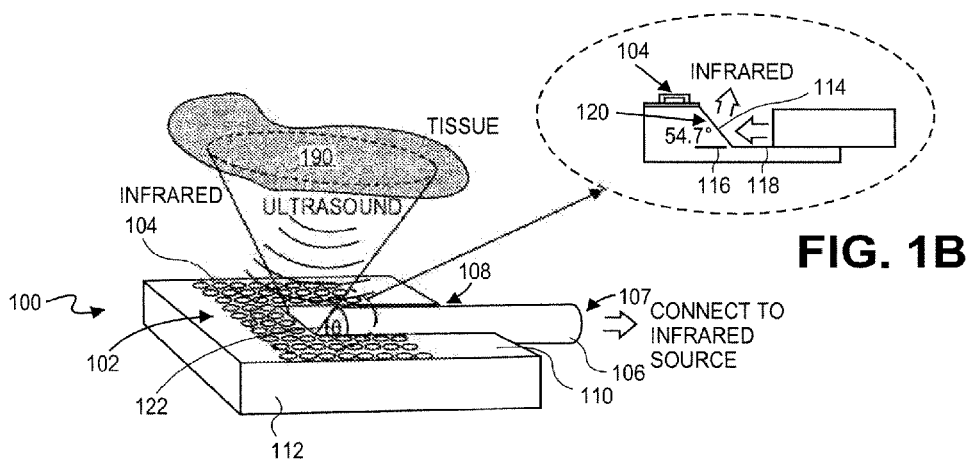
FIG. 1B
FIG. 1A
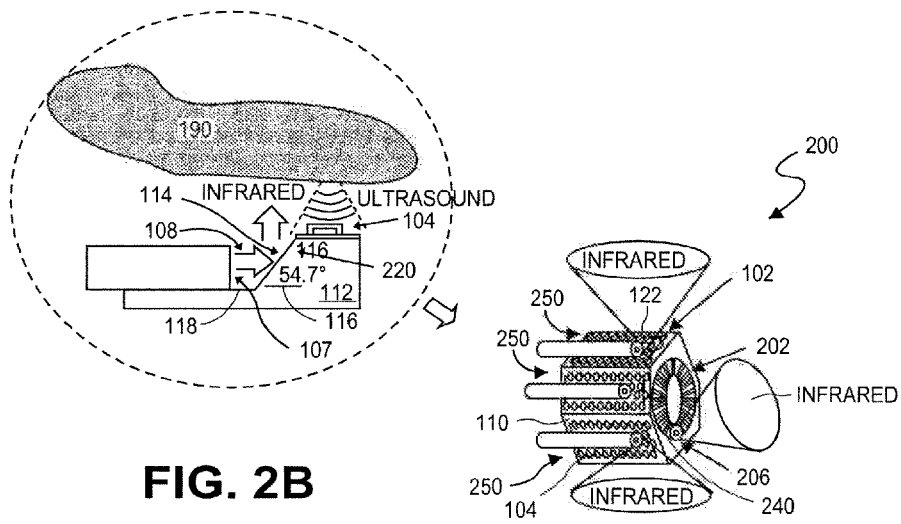
FIG. 2B
FIG. 2A

PHOTOACOUSTIC IMAGING DEVICES AND METHODS OF IMAGING

CROSS-REFERENCE TO RELATED APPLICATIONS

The present application is a continuation of U.S. patent application Ser. No. 12/747,428, filed Jun. 10, 2010, now U.S Pat. No. 8,529,454, which is a U.S. National Stage Application under 35 U.S.C. §371 from International Application No. PCT/US2008/086206, filed Dec. 10, 2008, which claims the benefit of priority under 35 U.S.C. §119(e) to U.S. Provisional Patent Application No. 61/007,023, filed Dec. 10, 2007 and U.S. Provisional Patent Application No. 61/032,947, filed Feb. 29, 2008, all of which are incorporated herein by reference in their entirety.

TECHNICAL FIELD

The present disclosure relates generally to imaging devices and methods and, more particularly, to photoacoustic imaging modules and methods for medical imaging and/or diagnosis.

BACKGROUND

Photoacoustic Imaging (PAI) is a non-invasive medical imaging technique capable of viewing anatomical structures inside the tissue. Photoacoustic imaging may deliver both a high spatial resolution and a high contrast in medical imaging applications. To the contrary, conventional pulse-echo ultrasound medical imaging does not deliver both a high spatial resolution and a high contrast due to the similar acoustic properties of different body tissue. Compared to X-ray, photoacoustic imaging is a safer technique because it is non-ionizing and does not affect the molecules in the body.

Photoacoustic imaging is a relatively new technology and has not found its way too much into the clinical arena for use on humans, like ultrasound imaging has been for the last 50 years. One of the primary reasons is that the hardware has been less than desirable. Photoacoustic imaging makes use of infrared-induced ultrasound for constructing images of a target object. In this imaging process, the object to be imaged is flashed with a short near-infrared pulse, for example, a pulse in the order of nanoseconds. The long wavelength of near infrared light allows light to penetrate deep into the tissue. As the light is absorbed by tissue chromophores such as hemoglobin in blood, the tissue heats up and expands through a process called rapid thermoelastic expansion. This instantaneous tissue expansion creates ultrasonic waves which can be received by an ultrasound detector array placed outside the body. The received acoustic signals can be interpreted using beamforming algorithms to generate 2D or 3D images of the target tissue. PAI take advantages of the high contrasts of optical imaging and the spatial resolution of pure ultrasound imaging.

Photoacoustic imaging makes use of the infrared absorption rate difference of different kinds of tissue to create high-contrast images. Thus, different tissue absorbs different amounts of the infrared radiation and transmits ultrasound signals with dissimilar magnitude, phase, and/or frequency. These ultrasound signals are received by a transducer, summed up, and analyzed to produce images of the target tissue.

In photoacoustic imaging of humans and other animals with red blood cells, hemoglobin plays an important role in enhancing the image contrast because hemoglobin has a very high optical contrast when near infrared radiation is applied. As a result, high-contrast imaging of blood-containing structures in tissue, such as tumors or blood vessels, is one of the unique characteristics of photoacoustic imaging. By making use of this blood concentration/content related optical absorption, photoacoustic imaging may be useful for identifying diseases and/or abnormalities related to blood, including bleeding and (early-stage) cancer tumors. Thus, doctors can use photoacoustic imaging to recognize many problems that are difficult to identify via other techniques, such as, for example, ultrasonic imaging. In addition to viewing anatomical structure, photoacoustic imaging is capable of detecting composition of tissue and functional activities of an organ based on blood related infrared absorption rate differences.

In summary, traditional ultrasound imaging has low contrast in soft tissue, because the acoustic properties of different soft tissues are very similar. Photoacoustic imaging, on the other hand, delivers a much better contrast than ultrasonic imaging. Photoacoustic imaging is based on OPTICAL absorption for contrast, which depends primarily on the absorption spectrum of the tissue on the near-infrared light. The information is carried in the ultrasonic waves which allows for 3D imaging. One-way propagation of ultrasound is used to carry the information back to the ultrasound receiver. For photoacoustic imaging of live human or animal's tissue with red blood cells, hemoglobin provides significant help in boosting the contrast ratio. Due to the difference of imaging mechanisms, photoacoustic imaging delivers significant higher image contrast than traditional ultrasound imaging. The differences are especially significant on imaging of blood containing organs, e.g., cancer tumors.

Some conventional tubular ultrasonic internal imagers use piezoelectric transducers for transmitting and receiving ultrasound. Piezoelectric transducers used for medical imaging typically operate at a voltage higher than 100V. This high operation voltage requirement makes it difficult to fit these piezoelectric imagers into a miniature wireless unit for capsule endoscope applications; a wireless capsule endoscope powered by a battery is barely capable of providing such a high voltage even with the help of sophisticated voltage-pump circuits.

Recently, capacitive micromachined ultrasonic transducers (CMUTs) emerged as a promising alternative for piezoelectric transducers for medical imaging. In the ultrasound transmission process, the membrane of a CMUT is generally biased with a d.c. voltage. An a.c. signal is superimposed on this d.c. bias to cause a time-varying deformation of the membrane. This membrane deformation stirs the ambient media and transmits ultrasound. In a reception process, the membrane is also biased with a d.c. voltage, typically smaller in magnitude than that required for the transmission process. The impinging ultrasound deforms the membrane and causes a change in capacitance which is read out by the control electronics. Generally, the ultrasound transmission process consumes much more power than a reception process. For wireless endoscopic applications, lowering the power consumption such that the ultrasonic imager can operate a longer time with a battery may be desirable for the feasibility of the technology.

Currently, one conventional practice for photoacoustic imaging uses a near-infrared laser to illuminate a target biological object. The laser may comprise, for example, a Q-switched Nd:YAG laser or a laser diode coupled to an optical fiber or a lens. A separately located ultrasonic transducer array is used to receive the ultrasound emitted by the tissue. This arrangement may facilitate exploratory experiments, but may not be suitable for clinical uses, since the relative positions between the infrared beam, the target tissue, and the ultrasonic transducer array have to be manually adjusted. The manual alignment/adjustment is time consuming and generally does not deliver the accuracy needed for clinical use. Thus, these systems are not friendly to end users like medical doctors.

In addition to non-invasive detection, photoacoustic imaging has been used in invasive diagnosis for which part or the whole imager system is placed inside the tissue or an organ to be examined. Since it is close to the target being explored, an invasive photoacoustic imager is able to pick up the ultrasound signal before it attenuates appreciably through the tissue. It may therefore provide a better signal-to-noise ratio and deliver an image quality not available from a non-invasive modality.

One example of an invasive photoacoustic imager is an imager used for intravascular diagnosis. Several different modalities have been proposed for intravascular photoacoustic imaging. For example, a commercial side-looking intravascular ultrasound (IVUS) head was tested for photoacoustic imaging of a blood vessel by illuminating the blood vessel from outside of the patient's body using an infrared laser. While preliminary phantom images were obtained with this approach, this setup has at least two drawbacks. First, due to decay and scattering of infrared light in the tissue, laser illumination from outside of the patient's body is generally insufficient in strength for the photoacoustic imaging process on vessels deep inside the body. Second, the obstruction/shadowing of illumination by the IVUS head itself and/or an organ like a bone may introduce a dead viewing angle which could block a significant amount of view.

A possible solution to the aforementioned problem may be to integrate the light source with the ultrasound transducers, thereby providing the infrared illumination from the imager. Such a concept has been utilized in a variety of photoacoustic imaging designs. For example, a front-looking photoacoustic imaging probe that integrates an optical fiber with a polymer ultrasound transducer for intra-arterial imaging has been prototyped. The imaging probe was made up of a 600 μm core diameter optical fiber with a focused polymer transducer element constructed around the core of the fiber at its tip. This device was demonstrated to be capable of receiving the ultrasound signals transmitted by a human's finger tissue and nail in a photoacoustic process. However, due to being equipped with only one single element instead of an array of ultrasound transducers, no actual imaging was achieved.

Another possible solution included a customized optical fiber head for infrared excitation and ultrasound reception. On this all-optical photoacoustic probe, a thermal-sensitive Fabry-Perot polymer film sensor was mounted at the end of an optical fiber for receiving the ultrasound transmitted by a target object in a photoacoustic process. The optical fiber was used to introduce infrared radiation from an external laser source to the target object for stimulation as well as to guide the reflected infrared radiation (which carries the ultrasound information) to an external signal processing optoelectronic unit. This device was designed to look at the forward direction in which the optical fiber tip is pointing and was incapable of side viewing.

The photoacoustic imaging devices of the present disclosure solve one or more of the problems set forth above.

SUMMARY OF THE INVENTION

The present disclosure relates to photoacoustic imaging modules for medical diagnosis. When tissue is stimulated with infrared light, the imaging module generates ultrasound through a rapid thermal-elastic expansion process. An array of ultrasonic transducers, which can be capacitive micromachined ultrasonic transducers (CMUT) or piezoelectric transducers, may be used to receive the ultrasound transmitted from the tissue. The infrared light for photoacoustic imaging may be provided via an array of light sources along the peripheral of this module, which can be an array of near-infrared laser diodes, light emitting diodes, or optical fibers (with connection to external light sources) mounted inside tilted recesses distributing along the peripheral of the frame. The module may be integrated into a wireless endoscope to create an internal imaging device that delivers better image contrast and operates at lower voltage and power. This device may therefore operate with a battery for a longer time.

In various aspects, the present disclosure is directed to a photoacoustic medical imaging device comprising a substrate, an array of ultrasonic transducers on the substrate, at least one groove etched on the substrate, at least one optical fiber, and at least one facet. Each optical fiber is disposed in one of the grooves. Each facet is etched in one of the grooves and coated with a layer of metal having high infrared reflectivity. Each optical fiber is configured to guide infrared light from a light source through the fiber and toward the respective facet. The facet is configured to reflect the infrared light toward a target.

According to some aspects of the disclosure, a photoacoustic medical imaging device may comprise a single substrate, a plurality of arrays of ultrasonic transducers on the single substrate, and a plurality of grooves etched on the substrate. At least one groove is associated with each array. The device may further include a plurality of optical fibers, wherein each optical fiber is disposed in one of the grooves. The device may also include a plurality of facets, wherein each facet is etched in one of the grooves and coated with a layer of metal having high infrared reflectivity. Each of the optical fibers may be configured to guide infrared light from a light source through the fiber and toward one of the facets, and the facets may be configured to reflect the infrared light toward a target.

In accordance with various aspects of the disclosure, a method of making a photoacoustic medical imaging device may include integrating a plurality of arrays of ultrasonic transducers on a single substrate, etching a plurality of grooves on the substrate, wherein at least one groove is associated with each array, and etching a facet in each one of said grooves. The method may further include coating each facet with a layer of metal having high infrared reflectivity and performing a photolithography process to delimit a photoacoustic imager, wherein the photoacoustic imager may comprise a plurality of the arrays. The method may also include etching the substrate to release the photoacoustic imager from a remainder of the substrate and placing at least one optical fiber in each of the grooves.

BRIEF DESCRIPTION OF THE DRAWINGS

FIG. 1A is a front perspective view of an exemplary photoacoustic imager in accordance with various aspects of the disclosure.

FIG. 1B is an enlarged cross-section view of the circled portion of FIG. 1A.

FIG. 2A is a side perspective view of an exemplary three-dimensional photoacoustic imager in accordance with various aspects of the disclosure.

FIG. 2B is an enlarged cross-section view of a portion similar to that shown in FIG. 1B.

DETAILED DESCRIPTION

Figure 3A:
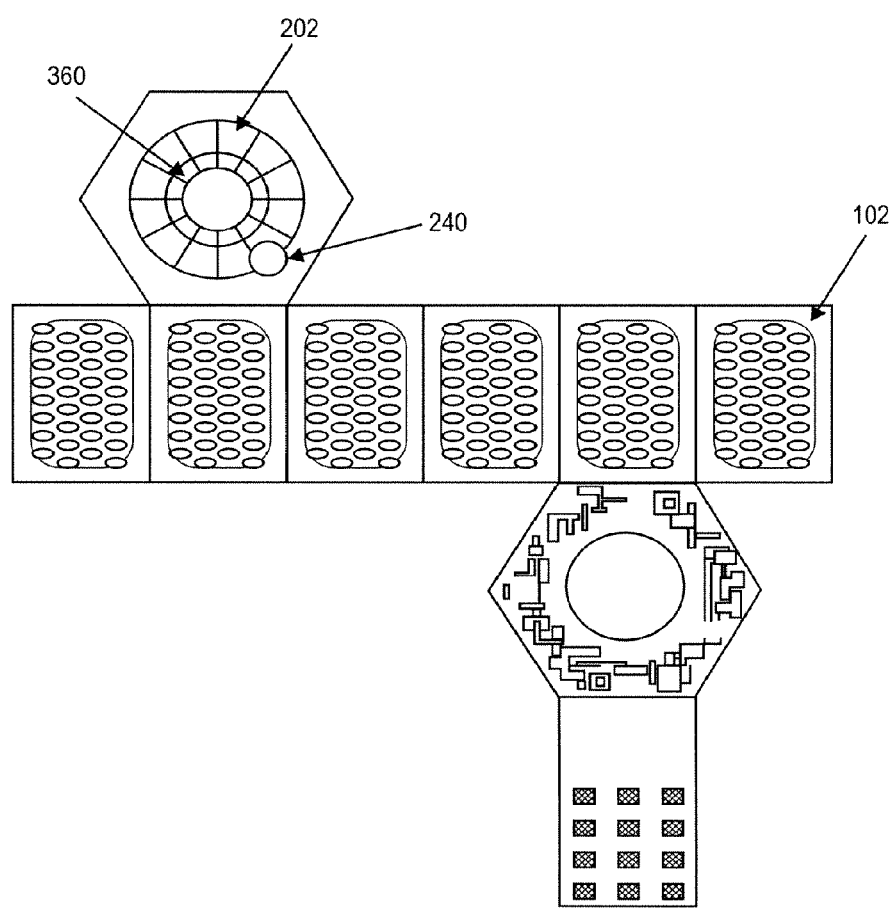
FIG. 3A is a top view of the three-dimensional photoacoustic imager of FIG. 2A in an unassembled configuration.

An exemplary embodiment of a photoacoustic imager 100 is shown in FIGS. 1A and 1B. According to various aspects of the disclosure, the photoacoustic imager 100 may comprise a single chip photoacoustic imager. The photoacoustic imager may include an array 102 of ultrasonic transducers 104, such as, for example, capacitive micromachined ultrasonic transducers (CMUTs) or piezoelectric ultrasound transducers, associated with a substrate 112, such as, for example, a silicon substrate. The imager 100 may include one, or an array of, optical fiber 106 configured to provide infrared illumination. For photoacoustic imaging, the power density of infrared light needed is in the order of milli-joules per square centimeter. A multi- or single-mode optical fiber is capable of delivering this power intensity.

The optical fiber 106 may be buried in a groove 108, for example, an anisotropically-etched V-groove, on a surface 110 of the silicon substrate 112. Infrared light may be guided through the optical fiber 106, out an end 107 of the fiber 106, and reflected by a facet 114 etched on the silicon substrate 112, which in turn casts the infrared light on the target tissue 190. According to some aspects, the silicon substrate 112 may comprise, for example, a (100) silicon substrate, and the facet 114 may comprise a (111) facet. The infrared light may be provided by an external light source (not shown) and guided through the optical fiber 106. The light source may comprise, for example, a Q-switched Nd:YAG laser, a laser diode coupled to an optical fiber or a lens, or the like.

Referring to the inset of FIG. 1B, the facet 114 may make an angle of substantially 54.7° with respect to a horizontal extension 116 of the bottom 118 of the groove 108. The facet 114 may be coated with a thin layer of metal 120, for example, silver or another metal of high infrared reflectivity, to enhance reflectivity of the facet 114 to the infrared light. The optical fiber 106 may comprise a diameter of about 125 µm and may have a core 122 comprising a diameter of about 5 µm.

This photoacoustic imager 100 does not require a strict dimension control on the V-groove 108, nor a high precision alignment between the optical fiber 106 and the V-groove 108. Different from the high precision alignment needed between optical fibers and other optical components in an optical fiber communication system, the alignment of the optical fibers to this photoacoustic imager platform is less critical. Minor misalignment between the optical fiber 106 and the reflection facet 114 will not affect the illumination function or the imaging capability of this photoacoustic imager 100. As the core 122 of the optical fiber 106 is relatively small compared to the diameter of the fiber 106 or the size of the facet 114, as long as the infrared light exits and end 107 of the fiber 106 and can cast on the (111) facet 114 inside the V-groove 108, minor misalignment will not introduce significant degradation to the function of this integrated photoacoustic imaging unit 100.

An exemplary embodiment of a three-dimensional photoacoustic imager 200 is shown in FIGS. 2A and 2B. The three-dimensional imager 200 may accommodate a plurality of photoacoustic imaging units 250 for panoramic viewing. According to various aspects, the photoacoustic imager 200 may comprise seven photoacoustic imaging units 250. A similar design for conventional pulse-echo ultrasound imaging has been previously achieved. Six of the seven imaging units 250 may define a 360° view about an axis 252. These six imaging units 250 may comprise, for example, six of the previously-described photoacoustic imagers 100.

For example, on the three-dimensional photoacoustic imager 200, a plurality of arrays 102 of ultrasonic transducers 104, such as, for example, capacitive micromachined ultrasonic transducers (CMUTs) or piezoelectric ultrasound transducers may be integrated on a single silicon substrate 112. In an exemplary embodiment, the three-dimensional photoacoustic imager 200 may include seven CMUT arrays 102, 202 for viewing seven different directions.

An array of grooves 108, for example, six V-grooves about 250 µm deep, may be anisotropically etched on a surface 110 of the substrate to accommodate a plurality of optical fibers 106, for example six fibers, for infrared coupling. Each groove 108 may include a facet 114 etched on the silicon substrate 112. An optical fiber 106 may be disposed in each groove 108 such that an end 107 of the fiber 106 can direct infrared light toward the facet 114, which in turn casts the infrared light on the target tissue 190.

According to some aspects, the silicon substrate 112 may comprise, for example, a (100) silicon substrate, and the facet 114 may comprise a (111) facet. The infrared light may be provided by at least one external light source (not shown) and guided through the optical fibers 106. The light source may comprise, for example, a Q-switched Nd:YAG laser, a laser diode coupled to an optical fiber or a lens, or the like.

Referring to FIG. 2B, the facets 114 may make an angle of substantially 54.7° with respect to a horizontal extension 116 of the bottom 118 of a respective groove 108. The facets 114 may be coated with a thin layer of metal 120, for example, silver or another metal of high infrared reflectivity, to enhance reflectivity of the facets 114 to the infrared light. Each of the optical fibers 106 may comprise a diameter of about 125 µm and may have a core 122 comprising a diameter of about 5 µm. These six arrays 102 may be configured to provide panoramic viewing of a target around a periphery of the imager 200.

As shown in FIG. 2A, one of the optical fibers 206 may be configured for a seventh viewing direction, i.e., front viewing. Infrared light for front-viewing may be guided through the optical fiber 206 extending through a hole 240 on a front-viewing transducer array 202, such as, for example, an annular CMUT array.

Figure 3C:
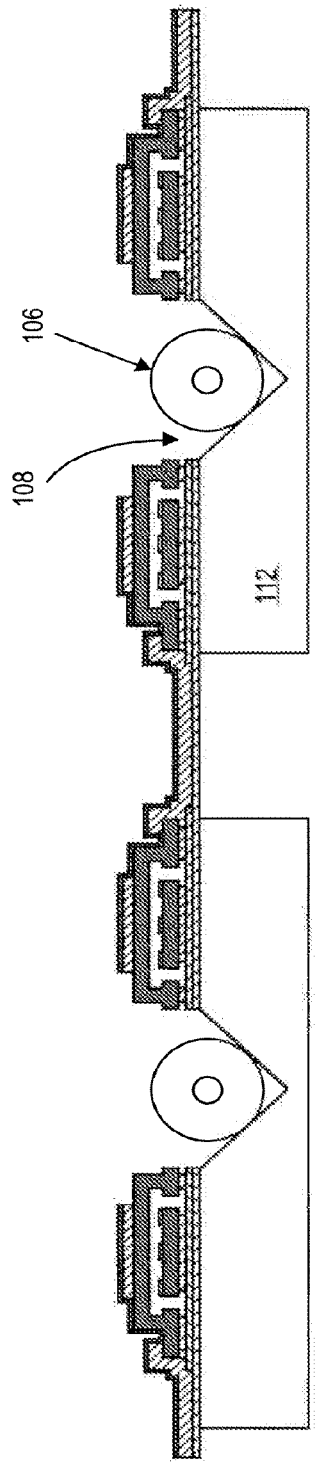
FIG. 3C is an enlarged cross-section view of the circled portion of FIG. 3B.
Figure 3B:
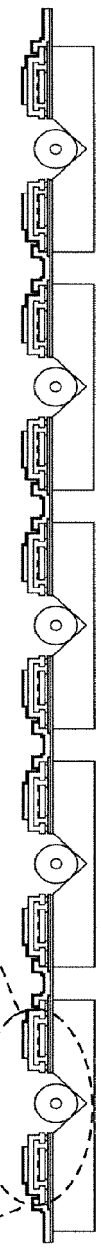
FIG. 3B is a cross-section view along line IIIB-IIIB of FIG. 3A.

Referring now to FIGS. 3A-3C, an exemplary method of making a three-dimensional photoacoustic imager is described. The method may commence with a polysilicon surface micromachining process for construction of CMUT arrays. Some details of the exemplary method are described in "A Monolithic Ultrasonic Transducer Array for Medical Imaging," IEEE Journal of Microelectromechanical Systems, vol. 16, pp. 1015-1024, October 2007, by the inventor of this disclosure and others, which is incorporated by reference in its entirety.

After passivating the CMUT arrays with a layer of biocompatible polymer, V-grooves 108 of appropriate width and depth, which is determined by the diameter of the optical fiber used, may be formed in the substrate using a wet or dry anisotropic etching, for example. The silicon substrate may then be tilted and a thin layer, for example, about 3000-5000 Å, of silver or another metal of high infrared reflectivity may be sputtered to coat the slanted silicon facets 114 inside the V-groove 108 at which the ends 107 of the optical fibers 106 are pointing. The metal-coated facets may function as mirrors to reflect infrared light from its original path directed from the fiber 106 toward the target tissue as shown in FIG. 2B.

According to some aspects, as the facets 114 delimit an end of V-grooves 108, each facet 114 may define a triangular mirror having a height of about 250 μm, for example, and a base width of about 350 μm, for example, which are both substantially greater than a diameter of a core of an optical fiber, which is typically about 5 μm. As a result, a misalignment of up to tens of microns between the optical fibers and the facets of the V-grooves 108 does not introduce much impact on the efficiency of reflecting the infrared light from the optical fibers 106 to the tissue.

The silicon substrate may then be flipped and glued to a carry wafer. The carry wafer and silicon substrate may include a plurality of CMUT arrays 102, 202 such that each carry wafer and silicon substrate can produce a plurality of photoacoustic imagers 200, each including seven arrays 102, 202.

A flood etching from the backside may be used to thin the wafer to approximately 250 μm, for example. A photolithography process may be performed on the backside to define an array of trenches, each about 40 μm—wide, for example, around a periphery of each CMUT array 102, 202. A deep silicon etching from the backside may then be used to open the trenches until they cut through the silicon substrate. A wet etching in acetone may then release each photoacoustic imager 200 (each containing seven CMUT arrays 102, 202) from the carry wafer. The planar arrays 102, 202 are then folded and/or assembled into a hexagonal imager prism, as shown in FIG. 3A, and the optical fibers 106, 206 are placed into the V-grooves 108 and the hole 240 in the front array 202. The front array 202 may include a hole 360 for accommodating, for example, a guiding wire, which may be used to direct the imager 200 into position during an interventional procedure. The optical fibers 106 may be glued in their positions using epoxy or any other appropriate medium.

Imagers in accordance with the various aspects of this disclosure may comprise a planar platform with a single CMUT/piezoelectric array for viewing in one direction or multiple CMUT/piezoelectric ultrasound transducer-fiber arrays monolithically integrated on a flexible substrate and assembled into a hexagonal prism for multi-directional viewing as an internal imager. The single-chip photoacoustic imagers of the disclosure can be implemented as hand-held platforms for operation outside of a patient's body and/or as miniature imager heads for intravascular and other invasive diagnosis.

Figure 4:
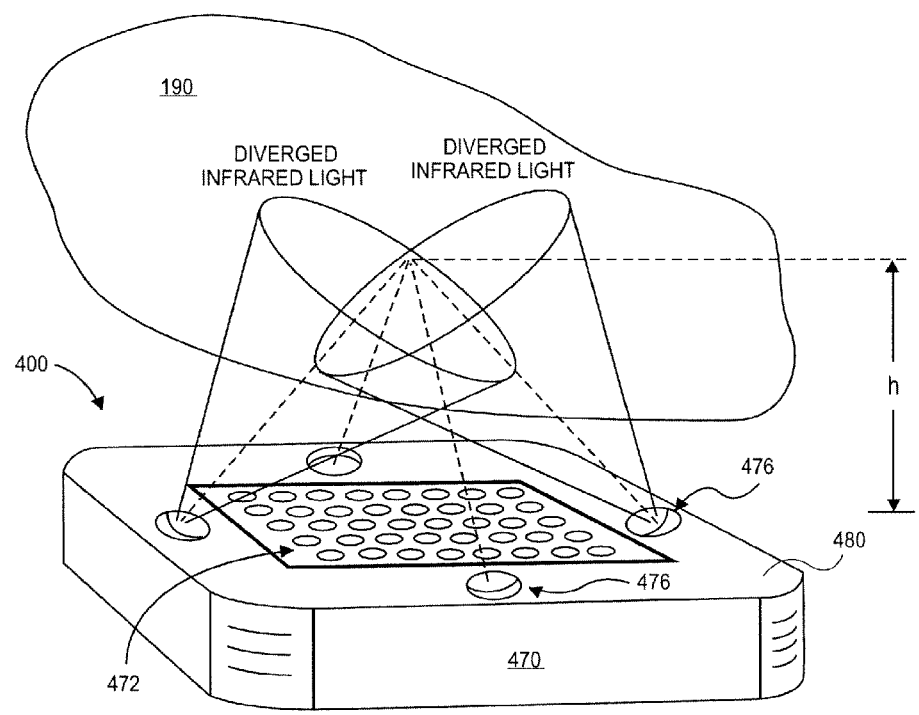
FIG. 4 is a front perspective view of an exemplary module for photoacoustic imaging in accordance with various aspects of the disclosure.
Figure 5A:
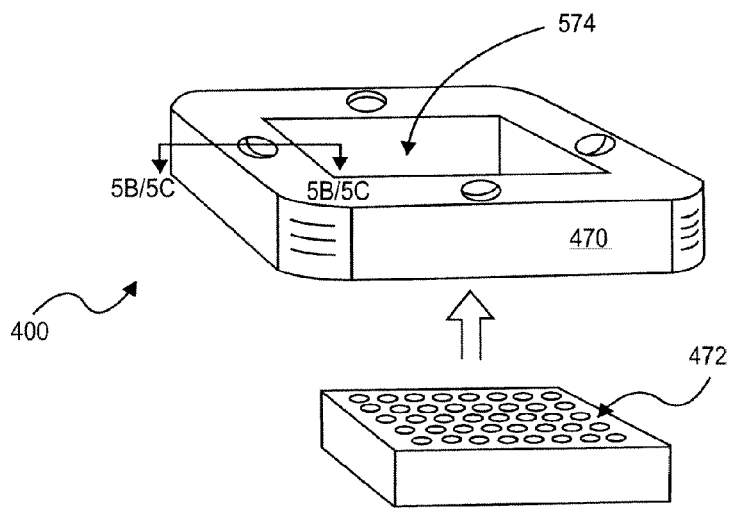
FIG. 5A is an exploded front perspective view of the exemplary photoacoustic imaging module of FIG. 4.

According to various aspect of the disclosure, FIG. 4 shows an exemplary module 400 for photoacoustic imaging. The module 400 includes a frame 470, which may be used to house the devices needed for photoacoustic imaging. The frame 470 may be made of plastic or other suitable materials. An array of ultrasonic transducers 472 may be disposed at a middle portion of the module 400. The ultrasonic transducers 472 are configured to receive ultrasound transmitted from the target tissue 190. As shown in FIG. 5A, the frame 470 may include a cutout 574 for receiving the array of ultrasonic transducers 472. According to some aspects of the disclosure, the array of ultrasonic transducers 472 may comprise capacitive micromachined ultrasonic transducers (CMUTs) associated with a substrate 512, such as, for example, a silicon substrate. In some aspects of the disclosure, the array of ultrasonic transducers 472 may comprise piezoelectric transducers.

The module 400 includes one or more light sources 476 arranged near a periphery of the frame 470. The light sources 476 may comprise near-infrared laser diodes, light emitting diodes, and/or optical fibers for providing infrared light for photoacoustic imaging. In the case of optical fibers, the fibers would be connected to external light sources (not shown), which emit light that is directed via the fibers. The frame 470 may include recesses 578 for receiving the light sources 476.

Figure 5C:
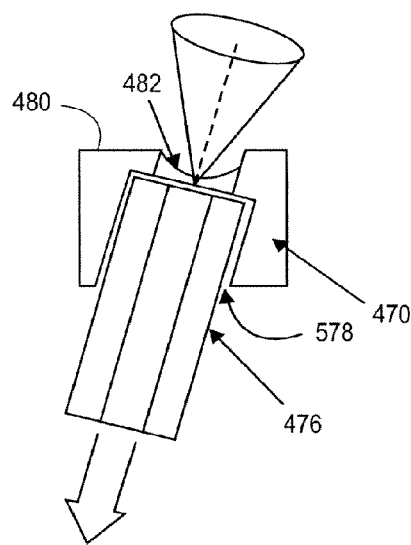
FIG. 5C is a cross-section view along line VB-VB of FIG. 5A illustrating an exemplary light source for the photoacoustic imaging module of FIG. 4 in accordance with various aspects of the disclosure.
Figure 5B:
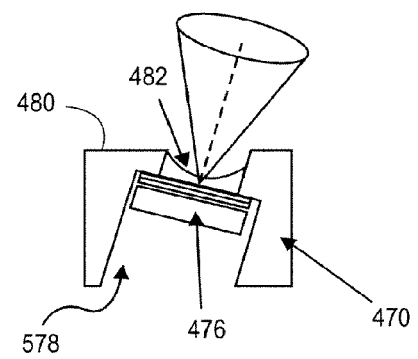
FIG. 5B is a cross-section view along line VB-VB of FIG. 5A illustrating an exemplary light source for the photoacoustic imaging module of FIG. 4 in accordance with various aspects of the disclosure.

As shown in FIGS. 5B and 5C, the recesses 578 may be angled with respect to a surface 480 of the frame 470 from which the light is emitted. For example, as illustrated, the recesses supporting the light sources can tilt toward the center of the platform such that the geometrical center of the target tissue gets the most illumination from the light sources 476. In some aspects, the ultrasound transducers 472 and the infrared light sources 476 may be integrated on one platform such that the relative position between the ultrasound transducer array 472 and the infrared light sources 476, as well as the depth h of the target tissue 190, are fixed and no manual alignment is needed for photoacoustic imaging.

FIG. 5B illustrates exemplary laser diode or light emitting diode light sources, while FIG. 5C illustrates an exemplary optical fiber light source. The ends of the recesses 578 at the surface 480 may include an optical lens 482 through which light passes from the light sources 476 toward the target tissue 190.

Although FIGS. 4 and 5A show an exemplary design with four light sources along the periphery of the frame, imagers consistent with this disclosure are not limited to four light sources. The imaging module 400 may include any number of light sources, more or less than four, capable of providing appropriate intensity of infrared illumination and these light sources may be distributed anywhere appropriate on the module 400. It should be appreciate that the imaging module 400 can also be used for both photoacoustic and ultrasonic imaging with co-registration. For example, because of the difference of ultrasound absorption spectrum between different tissue and/or materials (e.g., plaque or clot in the blood vessel) inside the body, the spectrum of reflected ultrasound (originally transmitted from the ultrasonic transducer array) can be used to identify composition and structure of the target structure being diagnosed. This may be a useful complement to photoacoustic imaging. This dual imaging approach may provide comprehensive diagnostic information not available from only one of these modalities alone.

An ultrasound generated by tissue in a photoacoustic process typically has a bandwidth of approximately 30 MHz.

Although a capacitive micromachined ultrasonic transducer (CMUT) delivers a relatively broader bandwidth than conventional piezoelectric transducers, its bandwidth may be insufficient for covering the whole spectrum for photoacoustic imaging. For a circular CMUT device with its membrane anchoring along its whole circumference, the resonant frequency (which primarily determines the central frequency of the CMUT) of the membrane can be determined by the following analytical Equation:

$$f_r = \frac{1}{2\pi}\sqrt{\frac{k}{m_e}} \cong \frac{2t_m}{\pi a^2}\sqrt{\frac{E+T}{1.8\rho(1-v^2)}}$$

where $t_m$ is the thickness of the membrane, a is the radius of the membrane, T is the internal stress, E is the Young's modulus, p is the density, and v is the Poisson ratio of the membrane material. From this equation, it can be seen that the smaller the membrane radius (with a fixed membrane thickness) or the thicker the membrane, the higher the central frequency. If an array of membranes of different radii (or thickness) is hybrid in an element as shown in FIG. 6, the spectrum of this element will be the superposition of each individual membrane as shown in FIG. 7.

Figure 6:
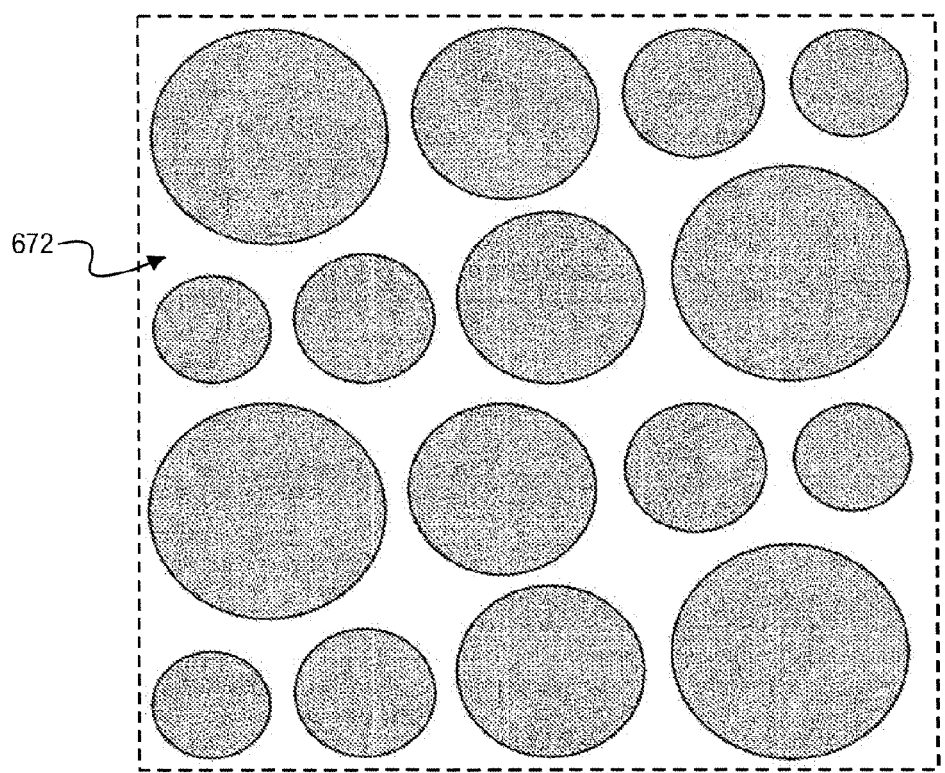
FIG. 6 is a top plan view of an exemplary CMUT element design in accordance with various aspects of the disclosure.
Figure 7:
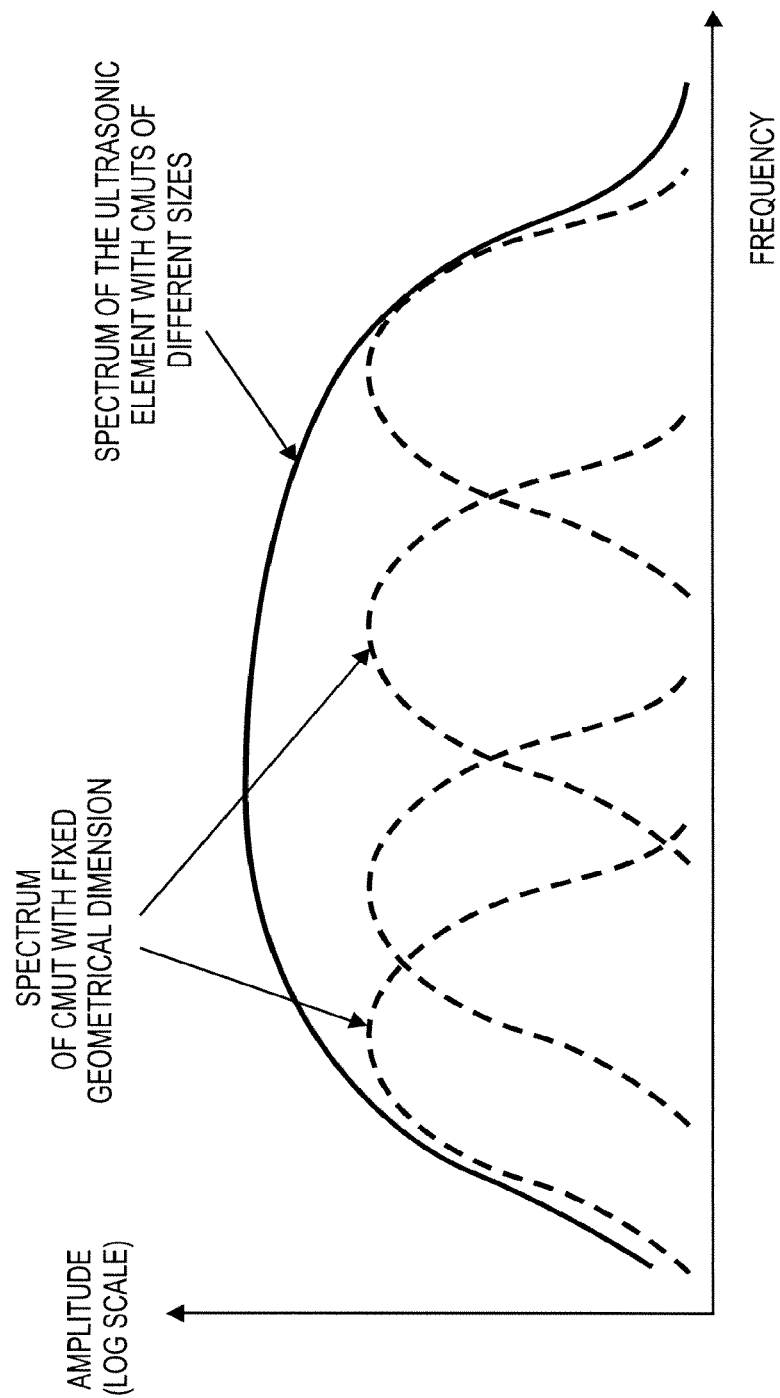
FIG. 7 is a graph showing the frequency response of an ultrasonic element comprising an array of transducers of different geometrical sizes.

FIG. 6 shows an exemplary CMUT element design that delivers a broad spectrum suitable for photoacoustic imaging. Instead of transducers of the same geometrical size, the transducer array 672 includes CMUTs of different sizes that are integrated in one element for receiving the ultrasound in the photoacoustic imaging process. As shown in FIG. 7, the spectrum of this hybrid element will be the superposition of that of CMUTs of different sizes and a broader spectrum can be achieved. Although in FIG. 6 an array of circular CMUT devices of different radii is illustrated, CMUTs of other geometrical shapes (e.g., square, rectangle, or the like) or a hybrid of different geometrical shapes with different sizes and/or membrane thicknesses are able to deliver a similar spectrum broadening effect and are included in this disclosure. The CMUT devices in such a hybrid element may be electrically connected in parallel.

Figure 8:
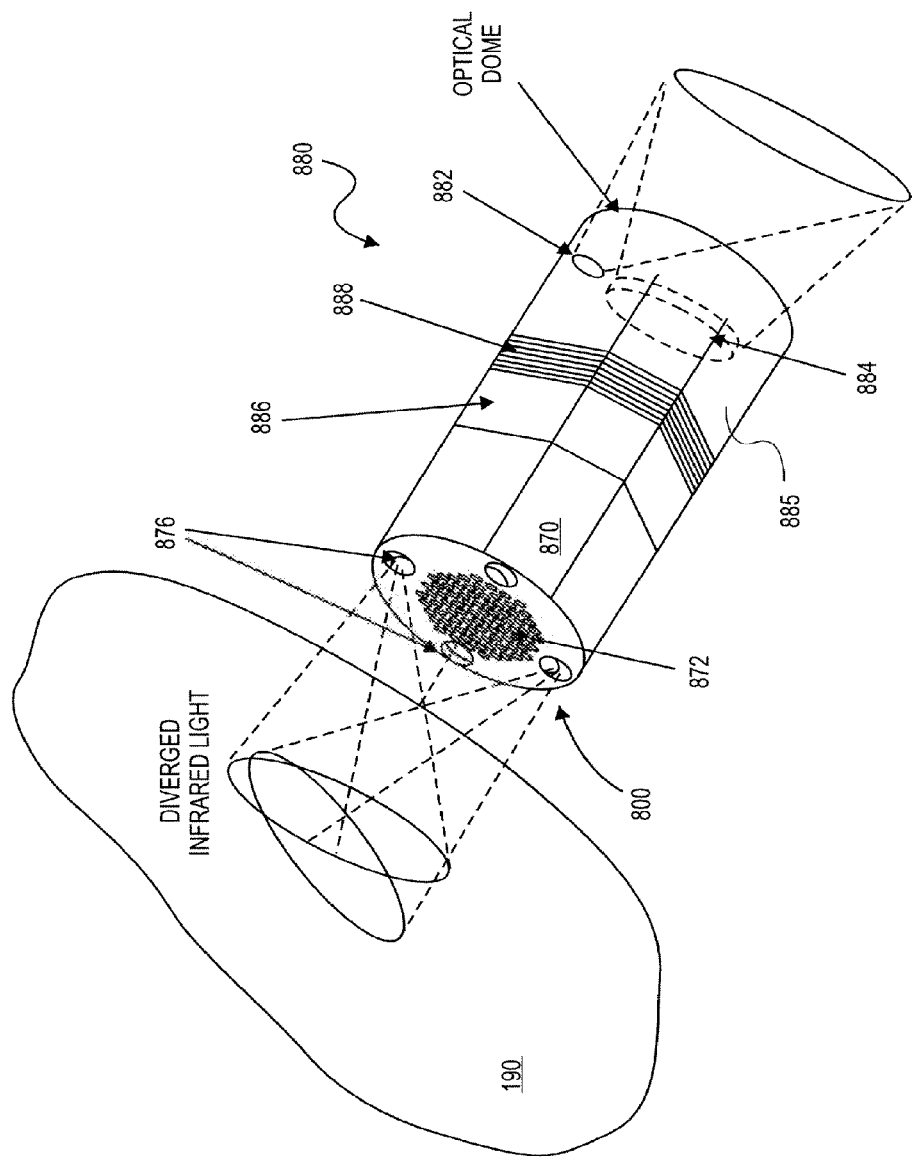
FIG. 8 is a front perspective view of an exemplary module of a wireless photoacoustic capsule endoscope in accordance with various aspects of the disclosure.

An exemplary embodiment for lowering the supply voltage of a wireless capsule endoscope is presented in FIG. 8. In FIG. 8, a wireless capsule endoscope 880 includes a photoacoustic imaging module rather than an ultrasound imaging module 800. The module 800 may include a frame 870, which may be used to house the devices needed for photoacoustic imaging. The frame 870 may be made, for example, of plastic or other suitable materials. On this photoacoustic system, in order to reduce the power consumption, the CMUT arrays 872 are used only for ultrasound reception. One or more light sources 876, for example, infrared laser diodes, light emitting diodes, and/or optical fibers, are used to stimulate the target tissue 190 that will generate ultrasound through a rapid thermal-elastic expansion process, as previously described. The capsule endoscope 880 may include a battery 886 configured to supply power to the CMUT arrays 872 and the light source diodes 876.

Laser diodes and light emitting diodes typically operate at a voltage lower than 10V which is significantly lower than that required for CMUT transmission. Typically, the quantum efficiency of a semiconductor diode is higher than 95% such that the electrical energy applied on the photonic devices (laser diodes and light emitting diodes) can be efficiently converted into infrared light for tissue stimulation and the subsequent ultrasound generation. Due to the fact that the reception process generally consumes less power and lower bias voltage than the transmission process for a CMUT device, this hybrid photoacoustic imaging system would operate at a lower power and voltage than a conventional ultrasonic imaging system. The system can therefore operate with the battery 886 for a longer time.

Figure 9A:
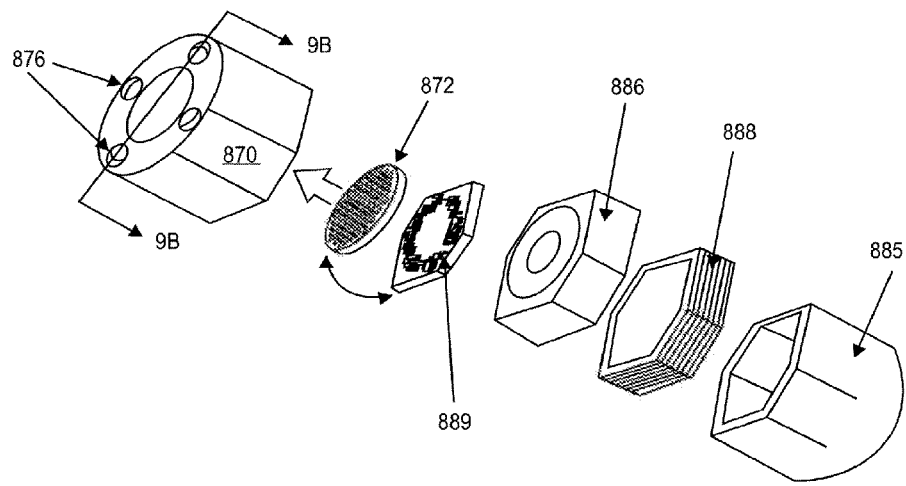
FIG. 9A is an exploded front perspective view of the exemplary wireless photoacoustic capsule endoscope of FIG. 8.

FIG. 9A shows the components of the exemplary wireless photoacoustic capsule endoscope 880, which may be used, for example, for gastro-intestinal tract diagnosis. In the photoacoustic capsule 880, multiple infrared light sources 876, such as, for example, laser diodes or light emitting diodes, may be integrated around the peripheral of an ultrasonic transducer array 872. The capsule endoscope 880 may include CMOS/DMOS beam-forming electronics 889 coupled with the ultrasonic transducer array 872 via, for example, flip-chip or wire bonding.

Figure 9B:
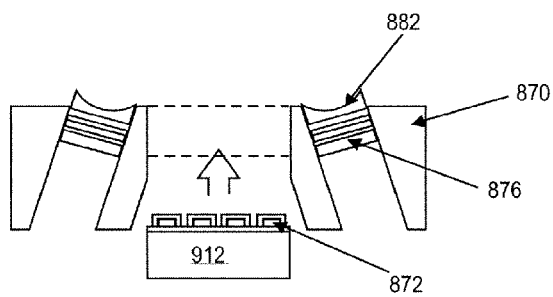
FIG. 9B is an enlarged cross-section view of the circled portion of FIG. 9A.

As shown in FIG. 9B, the ultrasonic transducer array 872 may be associated with a substrate 912, such as, for example, a silicon substrate. The light sources 876 may be tilted relative to a plane of the frame 870 toward the geometrical center of the target tissue 190 for achieving best illumination efficiency on the target tissue 190. Referring again to FIG. 8, an end of the capsule 880 opposite to the ultrasonic transducer array 872 may include a second light source 882 for illuminating a surface of a target tissue at, for example, a visible spectrum and a CMOS imager 884 capable of optically imaging a target tissue illuminated by the second light source 882 in order to perform medical diagnosis of the target tissue. The CMOS imager 884 and/or the second light source 882 may be housed in a shell 885 made, for example, of plastic or other suitable materials. The capsule 880 may also include a solenoidal inductor antenna 888 configured to transmit imaging data from the CMUT arrays 872 and/or the CMOS imager to receivers (not shown) outside of a patient's body.

Some advantages of using a photoacoustic imaging modality on this wireless capsule endoscope platform compared to its ultrasonic counterparts may include delivering better image contrast and/or operating at a lower voltage and power than a conventional ultrasonic imaging system, thus permitting the system to operate with a battery for a longer time.

It is noted that, as used in this specification and the appended claims, the singular forms "a," "an," and "the," include plural referents unless expressly and unequivocally limited to one referent. Thus, for example, reference to "a transducer" includes two or more different transducers. As used herein, the term "include" and its grammatical variants are intended to be non-limiting, such that recitation of items in a list is not to the exclusion of other like items that can be substituted or other items that can be added to the listed items.

It will be apparent to those skilled in the art that various modifications and variations can be made to the photoacoustic imagers and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A photoacoustic medical imaging device comprising:
   a substrate having a first surface and a second surface, the first surface being a planar surface different from the second surface;
   a first array of ultrasonic transducers on the first surface of the substrate;
   a first groove etched on the first surface of the substrate;
   a first optical fiber disposed in said first groove;
   a first facet, said first facet etched in said first groove and coated with a layer of a first metal having high infrared reflectivity, said first optical fiber being configured to guide infrared light from a light source through said first optical fiber and toward said first facet, said first facet being configured to reflect the infrared light toward a target such that at least one ultrasonic transducer of said first array of ultrasonic transducers is arranged to receive an ultrasound from the target in response to the infrared light directed toward the target, the target being external to the photoacoustic medical imaging device;

a second array of ultrasonic transducers on the second surface of the substrate;

a second groove etched on the second surface of the substrate;

a second optical fiber disposed in said second groove etched on the second surface; and a second facet etched in said second groove on the second surface and coated with a layer of a second metal having high infrared reflectivity, said second optical fiber being configured to guide infrared light from a second light source through said second optical fiber and toward said second facet, said second facet being configured to reflect the infrared light from the second light source external to the photoacoustic medical imaging device such that at least one ultrasonic transducer of the second array of ultrasonic transducers is arranged to operably receive an ultrasound in response to the infrared light directed external to the photoacoustic medical imaging device from the second facet.

2. The photoacoustic medical imaging device of claim 1, wherein said substrate comprises a silicon substrate.

3. The photoacoustic medical imaging device of claim 1, wherein said layer of the first metal comprises a layer of silver.

4. The photoacoustic medical imaging device of claim 1, wherein said first array of transducers comprises an array of capacitive micromachined ultrasonic transducers.

5. The photoacoustic medical imaging device of claim 1, wherein said first array of transducers comprises an array of piezoelectric ultrasound transducers.

6. The photoacoustic medical imaging device of claim 1, wherein said first groove is anisotropically etched on the substrate.

7. The photoacoustic medical imaging device of claim 1, wherein said first groove comprises a V-groove.

8. The photoacoustic medical imaging device of claim 1, wherein said first facet comprises a (111) facet.

9. A photoacoustic medical imaging device comprising:

a single substrate having a front viewing surface and having a plurality of surfaces defining a 360 degree view about an axis of the single substrate;

a plurality of arrays of ultrasonic transducers on the single substrate, an array of the plurality of arrays on each surface of the plurality of surfaces;

a plurality of grooves etched on the substrate, at least one groove associated with each said array of the plurality of arrays;

an array of ultrasonic transducers on the front viewing surface;

a plurality of optical fibers, each said optical fiber disposed in one of said grooves;

an optical fiber extending through the front viewing surface; and a plurality of facets, each facet etched in one of said grooves and coated with a layer of metal having high infrared reflectivity, each of said optical fibers being configured to guide infrared light from a light source through said fiber and toward one of said facets, said one facet being configured to reflect the infrared light toward a target such that at least one ultrasonic transducer is arranged to receive an ultrasound from the target in response to the infrared light directed toward the target, the target being external to the photoacoustic medical imaging device.

10. The photoacoustic medical imaging device of claim 9, wherein said substrate comprises a silicon substrate.

11. The photoacoustic medical imaging device of claim 10, wherein said substrate comprises a flexible silicon substrate.

12. The photoacoustic medical imaging device of claim 9, wherein said layer of metal comprises a layer of silver.

13. The photoacoustic medical imaging device of claim 9, wherein each of said arrays of the plurality of arrays of ultrasonic transducers comprises an array of capacitive micromachined ultrasonic transducers.

14. The photoacoustic medical imaging device of claim 9, wherein each of said arrays of the plurality of arrays of ultrasonic transducers comprises an array of piezoelectric ultrasound transducers.

15. The photoacoustic medical imaging device of claim 9, wherein each of said plurality of grooves is anisotropically etched on the substrate.

16. The photoacoustic medical imaging device of claim 9, wherein each of said plurality of grooves comprises a V-groove.

17. The photoacoustic medical imaging device of claim 9, wherein the facet comprises a (111) facet.

18. The photoacoustic medical imaging device of claim 9, wherein said array of ultrasonic transducers on the front viewing surface is an annular array.

19. A method of making a photoacoustic medical imaging device, comprising:

integrating a plurality of arrays of ultrasonic transducers on a single substrate, each array on a different surface of the single substrate;

etching a plurality of grooves on the substrate, at least one groove being associated with each said array;

etching a facet in each one of said grooves;

coating each facet with a layer of metal having high infrared reflectivity;

performing a photolithography process to delimit a photoacoustic imager, said photoacoustic imager comprising a plurality of said arrays;

etching the substrate to release said photoacoustic imager from a remainder of the substrate; and placing at least one optical fiber in each of said grooves, wherein the ultrasonic transducers, the facets, and the at least one optical fiber are arranged such that at least one ultrasonic transducer is arranged to receive an ultrasound from a target in response to infrared light from the at least one optical fiber to its corresponding facet directed toward the target, the target being external to the photoacoustic medical imaging device.

20. The method of claim 19, wherein the step of etching a facet comprises etching a (111) facet.

* * * * *